United States Patent [19]

Bennett

[11] Patent Number: 4,743,446

[45] Date of Patent: May 10, 1988

[54] LIVER FLUKE ANTIGENS DERIVED FROM JUVENILE FASCIOLO ORGANISMS

[75] Inventor: Clive E. Bennett, Shirley, England

[73] Assignee: National Research Development Corporation, England

[21] Appl. No.: 897,534

[22] PCT Filed: Dec. 20, 1985

[86] PCT No.: PCT/GB85/00594

§ 371 Date: Aug. 5, 1986

§ 102(e) Date: Aug. 5, 1986

[87] PCT Pub. No.: WO86/03680

PCT Pub. Date: Jul. 3, 1986

[30] Foreign Application Priority Data

Dec. 21, 1984 [GB] United Kingdom ............... 8432401

[51] Int. Cl.$^4$ .................. A61K 39/00; G01N 33/53
[52] U.S. Cl. .................................. 424/85; 424/88; 435/68; 530/395
[58] Field of Search ................... 435/68; 530/395; 424/88, 85

[56] References Cited

U.S. PATENT DOCUMENTS 4,416,866  11/1983  Strand ............................. 424/9 X

FOREIGN PATENT DOCUMENTS 011438A   5/1980  European Pat. Off. .
0044710   1/1982  European Pat. Off. .
0142345   5/1985  European Pat. Off. .
83/00929  3/1983  PCT Int'l Appl. .
85/02909  7/1985  PCT Int'l Appl. .

OTHER PUBLICATIONS

Immunology, Weir, 4th Ed. (1977), pp. 21-23.
I. J. Sinclair et al., Res. Vet. Sci., 16, 320-327 (1974).
C. E. Bennett, Parasitology, 77, 325-332 (1978).
C. E. Bennett, G. W. P. Joshua and D. L. Hughes, J. Parasitol, 68, 791-795 (1982).
T. J. Hayes et al., J. Parasitol., 58, 1103-1105 (1972).
J. C. Boray, Annals of Tropical Medicine and Parasitology, 61, 439-450 (1967).
M. J. Howell et al., International Journal of Parasitology, 9, 41-45 (1979).
M. J. Howell, J. Parasitol, 65, 817-819 (1979).
R. M. Sanderson and M. J. Howell, Res. Vet. Sci, 29, 255-259 (1980).
J. G. Ross, J. Helminthology, 41, 393-399 (1967).
N. J. Campbell et al., Int. J. Parasitol., 7, 347-351 (1977).
J. K. Dineen et al., Int. J. Parasitol, 8, 173-176 (1978).
G. B. B. Mitchell et al., Res. Vet. Sci., 30, 343-348 (1981).
Biological Abstracts, 66, 71066 (1978).
R. Taillez, Biologie Medicale, 59, 183-287 (1970), with translation of the summary on pp. 277-279.

*Primary Examiner*—Howard E. Schain
*Attorney, Agent, or Firm*—Jacobs & Jacobs

[57] ABSTRACT

It has been a problem to combat the liver fluke parasite in ruminant animals such as sheep and cattle. The present invention provides antigens having specificity for the juvenile stage of the organism. They are defined as obtainable from juvenile Fasciola, preferably *F. hepatica*, organisms by either of two closely related methods. In both methods crude antigen is extracted from juvenile Fasciola organisms and used to raise an antiserum (by injection into rabbits for example). The antiserum is then reacted with adult Fasciola antigens. An adult antigen—adult antibody complex is formed, leaving the other components of the antiserum including juvenile specific antibodies. The juvenile specific antibodies are separated from the complex by spinning and "Millipore" filtering. This is followed either by (1) separating IgG components, including specific IgGs, e.g. on a protein A column or (2) subjecting the post-absorption antiserum to immunoelectrophoresis against crude juvenile-specific antigens, and raising an antiserum against the antigen component of this complex. After step (1) or (2), the juvenile-specific antibodies (purified IgGs or antiserum) are used to purify crude juvenile Fasciola antigens. It is possible to omit step (1), in which case post-absorption antiserum is immunoglobulins of all classes are used in this step. Free antigen is liberated from the material bound to the column.

The invention also includes a fragment of the antigen carrying a juvenile-specific antigenic determinant, a vaccine comprising the antigen or fragment thereof together with an adjuvant or carrier, and monoclonal and polyclonal antibodies to the antigen or antigenic determinant.

25 Claims, 1 Drawing Sheet

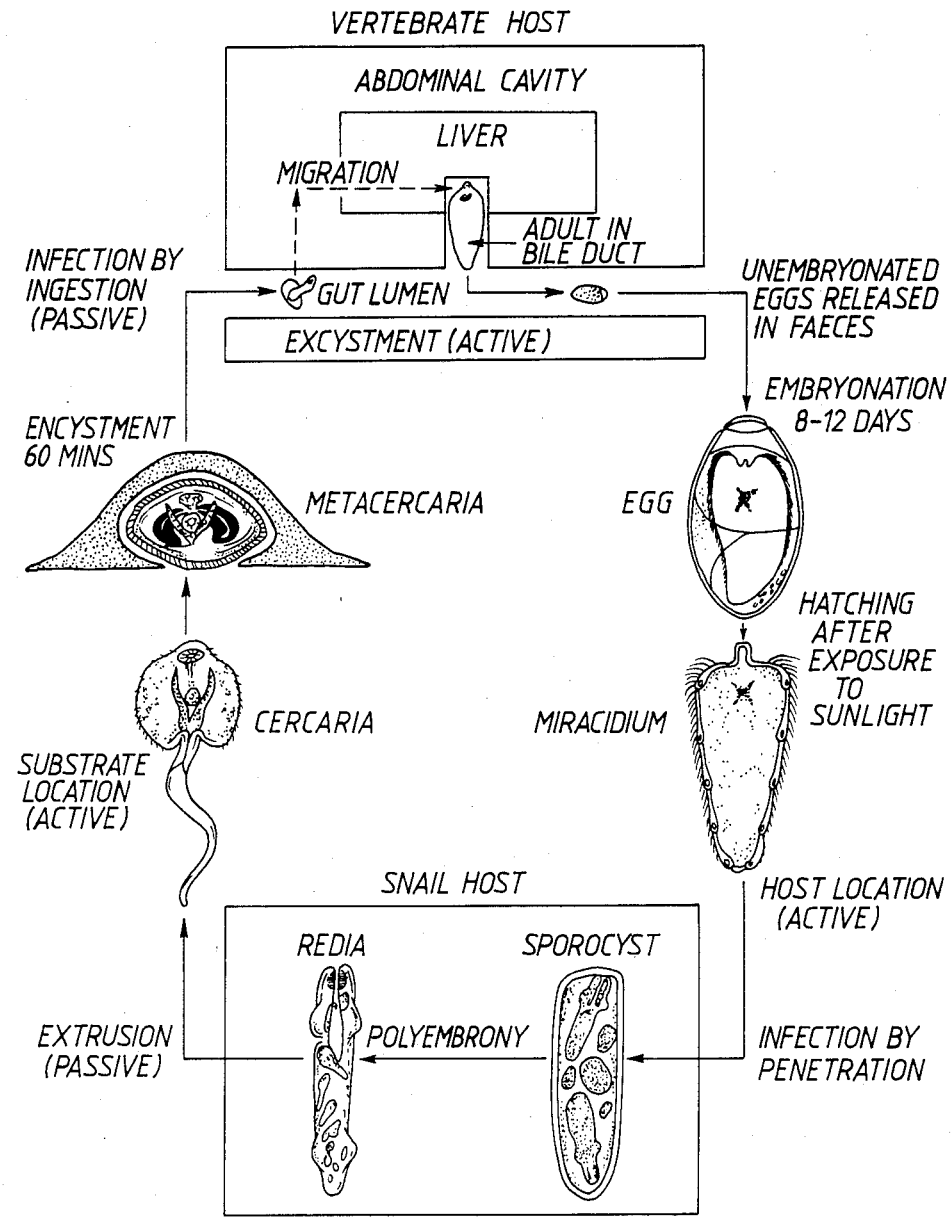
LIFE CYCLE OF FASCIOLA HEPATICA

LIVER FLUKE ANTIGENS DERIVED FROM JUVENILE FASCIOLO ORGANISMS

BACKGROUND OF THE INVENTION

1. Field of the Invention

This invention relates to antigens produced by the liver fluke organism Fasciola.

2. Brief Description of the Drawing

The accompanying drawing shows schematically the life cycle of *Fasciola hepatica*.

3. Description of Prior Art

*Fasciola hepatica* infections in cattle and sheep are reported to be responsible for losses due to poor growth and low milk yields valued in £ 1974 at (40 million per annum in the UK alone. It is also known that liver fluke increases susceptibility to salmonellosis in cattle. *F. hepatica* infections are also a serious problem in sheep, and increase susceptibility to "Black disease" caused by *Clostridium oedematiens*.

*F. hepatica* is a form of parasitic worm and has a complex life cycle involving more than one host which can more easily be understood from the accompanying drawing. The mature (adult) flukes reside in the bile ducts of a vertebrate host (cattle, sheep, etc.), from which eggs pass into the intestine and eventually onto pastures in faeces. After embryonation, miracidia are formed which hatch to infect certain species of snails (the second host). Asexual reproduction occurs in the snail and after some weeks the pre-infective form of fluke, known as cercariae, is released. A single miracidium typically gives rise to 200–600 cercariae. The cercariae anchor themselves to suitable substrates such as grass and secrete refractory coats or cysts. This process is called encystment. The encysted stage is known as a metacercaria and it is in this form that the parasite enters the vertebrate host, thereby infecting it. After ingestion by the vertebrate host, the juveniles emerge from their metacercarial cysts in the small intestine (a process known as excystment). The emergent free juveniles are hereinafter referred to as 0-day juveniles, to indicate the infective stage of the juveniles, at which they are ready to infect the animal. In this specification the "juvenile" stage means all stages from immediately before infection up to 4 days post infection (p.i.) in mice. (The length of the juvenile stage varies from one animal species to another). The juveniles migrate across the peritoneal cavity to the liver and thence to the bile duct, wherein they mature to adulthood.

Although there are many good chemotherapeutic agents available to combat liver flukes, the majority are ineffective against the earliest stages of a primary infection. Since primary infections often cause chronic, sometimes acute, disease, it would be advantageous to immunise the animals to protect against the earlier stages of primary infection. Dead adult flukes are ineffective, see K. B. Sinclair et al., Res. Vet. Sci. 16, 320–327 (1974). These observations have led to the hypothesis that a change in surface antigens occurs during the growth and development of *F. hepatica*. The juvenile and adult forms of fluke have a tegument, which includes a surface cytoplasmic layer connected to sub-muscular cellular regions by cytoplasmic tubes. The structure and cellular composition of the tegument changes with maturation of the fluke. The cytoplasmic layer has on its surface a plasma membrane which has on it a glycoproteinaceous surface layer which is known as the glycocalyx. The newly emerged 0-day stage juvenile flukes (NEJs) possess a glycocalyx specific to the juvenile stage, which is subsequently shed and exchanged for another type of glycocalyx before adulthood. The fluke replaces the shed layer after a short period by secretions from the tegument. It therefore changes the outermost surface which it presents to the vertebrate host and therefore the surface antigens which have stimulated an immune reaction in the host. It is thought that by this means the parasite evades immune attack, since by the time that the host has been stimulated to produce antibodies to the juvenile stage specific surface antigens presented, the fluke has changed its surface. In this way, a primary infection of fluke may evade the immune response for long enough to enter the liver parenchyma (a relatively protected and nutritious environment where the flukes of a primary infection are thought to avoid immune attack by turnover of the glycocalyx i.e. continuously sloughing off).

It will be evident from the above account that the formulation of a vaccine against *F. hepatica* infection is likely to be very difficult. An early paper supporting the above hypothesis is by Dr. C. E. Bennett, the present inventor, in Parasitology 77, 325–332 (1978). Antiserum against adult *F. hepatica* raised in rabbits reacted with the surface coat of formaldehydefixed adult flukes of both rat and mouse origin, as demonstrated by an indirect fluorescent antibody test (IFAT). A lack of reaction with live flukes indicated an active turnover of the surface antigen. Bennett also found that the adult antiserum did not react with fixed newly-excysted juveniles (NEJs), when they were very young viz. at 1 or 2 days post-infection (p.i.). At 5 days p.i. or older they did react. The existence of juvenile antigens was later demonstrated by the inventor, Dr. C. E. Bennett, with the valuable assistance of Mr. G. W. P. Joshua and Dr. D. L. Hughes, J. Parasitol, 68, 791–795 (1982). In this demonstration rabbits were injected with a crude preparation of antigens of metacercariae of *F. hepatica*, generating antibodies to a full range of somatic antigens. This mixture of antibodies was then "back-absorbed" with adult stage antigen (recovered from infected rats) and the antigen-antibody precipitate was removed. Thereby, all the antibodies to general somatic antigens present throughout maturation were precipitated, leaving an antiserum hypothetically containing anti-juvenile antibodies. This antiserum was tested for reaction with juvenile flukes of varying ages, using an IFAT. Freshly excysted 0-day juveniles gave a strong positive reaction. The degree of reaction fell with increasing age of the flukes under test, i.e. up to 4 days post infection in mice. This paper by Bennett et al. supports the postulate that there are juvenile-specific antigens, but, as the authors specifically say in their paper at page 794, right-hand column, does not indicate that juvenile-specific antigens are functional in stimulating immunity. Nor does it describe the preparation of antigens.

The literature is unclear on the issue of whether early or juvenile-specific antigens stimulate immunity. T. J. Hayes et al., J. Parasitol 58, 1103–1105 (1972) found that rats already infected with liver fluke were immune to reinfection by live metacercariae. This indicated that the immunological memory of the host, at least in rats, includes any juvenile antibody component that there might be. This was in contrast to J. C. Boray, Annals of Tropical Medicine and Parasitology 61439–450 (1967) who challenged liver fluke-free and infected sheep with live metacercariae and concluded that there was no appreciable difference between the two groups of sheep as judged by number of flukes excreted, clinical symptoms or pathology.

M. J. Howell et al., International Journal of Parasitology 9, 41–45 (1979) produced an antibody-antigen precipitate in vitro, by culturing the serum of liver fluke-infected rats with metacercariae. Vaccinations of rats with the precipitate in Freund's Complete Adjuvant (FCA) confirmed a significant degree of protection against an oral challenge with metacercariae in one experiment but no significant difference over the control in the other experiment. Subsequently Howell confirmed protection in Wistar rats, with modifications only to the route of immunisation His results showed significant levels of protection, 87% and 63% in separate experiments. In his first experiment 5 out of 6 rats vaccinated were completely protected showing no signs of liver damage or enlarged bile ducts. In his second experiment 2 out of 6 rats vaccinated similarly showed no signs of liver damage. See Journal of Parasitology 65, 817–819 (1979).

The above method of immunisation, involving use of an immune complex, was followed up in sheep, R. M. Sanderson and M. J. Howell, Res. Vet. Sci. 29. 255–259 (1980). Sheep were injected intramuscularly with a mixture of FCA and the complex obtained from in vitro culture of excysted metacercariae (in effect NEJs) and the serum of liver fluke-infected sheep. However, no protection was conferred on the sheep.

It is known from field observations that sheep and cattle do develop natural immunity to reinfection by liver fluke, see e.g. J. G. Ross, Journal of Helminthology 41, 393–399 (1967). There is experimental evidence of the role of the immune system, in that sheep can be made to develop immunity to liver fluke by the T-cell stimulant levamisole. Levamisole-treated sheep were infected with *Cysticercus tenuicollis*, challenged intra-ruminally with liver fluke metacercariae, and found to have a substantial level of resistance to liver fluke infection. See N. J. Campbell et al., Int. J. Parasitol. 7, 347–351 (1977) and J. K. Dineen et al., Int. J. Parasitol. 8, 173–176 (1978). G. B. B. Mitchell et al., Res. Vet. Sci. 30, 343–348 (1981) found that sheep first infected with nematodes (having no biological similarity to *F. hepatica*) and then treated with levamisole acquired immunity to *F. hepatica*. These authors speculated that an immunosuppressive component is involved in the pathogenesis of live fluke infection and that levamisole acts to correct the suppression.

The European patent Office Search Report RS 71916 GB on the priority UK application has cited four references, which will be briefly reviewed.

Biological Abstracts 75 72780 (1983) is an abstract of the Bennett et al. paper referred to above.

Chemical Abstracts 73 128965t (1970) abstracts R. Tailliez et al, Biologie Medicale 59, 183–287 (1970). The paper reviews immunological work on *F. hepatica* and reports the isolation and purification from adult *F. hepatica* of five immunologically active fractions in the fluke.

European patent Specification 11438A (Vaccines International Limited) describes a fascioliasis vaccine, especially for bovine administration, comprising irradiated metacercariae of *Fasciola gigantica* (which is the causative agent of fascioliasis in cattle in Africa). However, the previous attempted use of irradiated metacercariae for vaccination of sheep against *F. hepatica* was unsuccessful according to Biological Abstracts 66 71066 (1978) abstracting N. J. Campbell et al., Vet. Parasitol 4, 143–152 (1978).

PCT Application WO 83/00229 (The John Hopkins University) relates to diagnosis of fluke infections, and a method of passive vaccination which comprises administering monoclonal antibodies defined by their hybridoma cell lines. It is described in detail by reference to schistosomes, i.e. parasites of the genus Schistosoma, and is "premised on the discovery that the membrane of flukes in all growth phases, including eggs, contain two major glycoprotein molecules", referred to as fluke spine glycoproteins. It is suggested that *F. hepatica* and *F. gigantica* can be detected analogously.

SUMMARY OF THE INVENTION

The present invention is based on the finding that certain antigen substances can be extracted from liver flukes and are antigens of the juvenile stage, some of which are surface antigens, and that such juvenile-specific antigens (JSAs) do stimulate immunity and are therefore useful in vaccination of animals susceptible to liver fluke. They are defined as obtainable from juvenile Fasciola, preferably *F. hepatica*, organisms by either of two closely related methods. In both methods a crude antigenic extract of 0-day juvenile Fasciola is used to raise an antiserum. The antiserum is then back-absorbed with adult Fasciola antigens in a manner similar to that already described by C. E. Bennett et al., supra. An adult antigen - adult antibody complex is thereby formed, leaving the other components of the antiserum comprising juvenile-specific antibodies, unabsorbed. The juvenile-specific antibodies are then separated from the absorption product, i.e. from the antigen-antibody complex and other material. This can be done in various ways, giving juvenile-specific antibodies. These antibodies are then made insoluble, i.e. linked to a solid support material. They are then reacted with fresh crude 0-day juvenile Fasciola antigenic extract. Because of their history of preparation, these antibodies have a high specificity for the juvenile antigen, and therefore react predominantly with juvenile antigen, leaving free in solution any other antigens present in the crude juvenile Fasciola antigenic extract. The resultant juvenile antibody—juvenile antigen complex is then treated to liberate the antigen.

Once juvenile-specific antigens have been obtained in the above manner they can be used to prepare juvenile-specific monoclonal antibodies by conventional hybridoma technology, which in turn can be used to extract juvenile-specific antigens from juvenile Fasciola.

The invention is not limited to juvenile-specific antigens when prepared as described herein, but, rather, extends to those antigens howsoever prepared. The description herein of their preparation serves to identify them as obtainable by, but not necessarily obtained by, the described routes.

The invention also includes a fragment of the antigen carrying a juvenile-specific antigenic determinant, a vaccine comprising the antigen or fragment thereof together with an adjuvant or carrier, and monoclonal and polyclonal antibodies to the antigen or antigenic determinant.

DESCRIPTION OF THE PREFERRED EMBODIMENTS

In one preferred embodiment the antigens of the invention are obtainable from a crude antigenic extract of 0-day juvenile *Fasciola hepatica* organisms by raising an antiserum to the juvenile organisms, absorbing this antiserum with antigens extracted from adult *Fasciola hepatica* organisms, thereby forming an adult antigen - adult antibody complex and leaving other components of the antiserum unabsorbed, separating immunoglobulin components of the unabsorbed antiserum from the adult antigen - adult antibody complex, insolubilising the immunoglobulins, purifying a crude extract of 0-day juvenile *Fasciola hepatica* antigens by reacting them with the insolubilised immunoglobulins to form an antigen-antibody complex and liberating the juvenile-specific antigen from the complex. The *F. hepatica* organisms subjected to this method yielded a product which was believed to be proteinaceous and comprised substances of various molecular weight as reported hereinafter in the Examples. All such molecular weights are approximate, probably to plus or minus 1,500.

The step of absorption by adult antigen gives a product which contains unreacted antibody and, since adult antibody has already been absorbed, the unreacted material comprises any juvenile antibody which is juvenile-specific, i.e. is not reactive with adult antibody. To clean up the juvenile-specific antibody, it is centrifuged and filtered to remove immune complexes and conveniently passed down a column of insolubilised protein A. Protein A has an affinity only for the major immunoglobulins $IgG_1$, $IgG_2$ and $IgG_4$. The column therefore contains a protein A -IgG complex in which some of the IgGs are juvenile-specific antibodies. The IgGs are liberated from the column by flushing it with an appropriate solvent, e.g. acetic acid. The protein A column step could be omitted if desired or replaced by an anti-rat or -rabbit immunoglobulin affinity gel as appropriate, thereby retaining all immunoglobulin classes and sub-classes, possibly leading ultimately to recovery of further antigens.

In the next step, the IgG antibodies are bound to an insoluble support such as an agarose gel activated for covalent bonding of the antibody. This column is then used to purify the crude 0-day juvenile fluke antigen, which is conveniently the same material as was used in the very first step. Although this material was derived from a juvenile stage of the fluke, it contains other antigens and is generally a highly impure material. The resultant antibody-antigen complex on the column is then treated to remove the juvenile-specific antigen in the liquid phase from the solid phase antibody.

A second embodiment of the invention differs from the first only in the method by which the juvenile-specific antibody in the absorbate is cleaned and amplified. The absorbate (see above) is reacted with protein components of crude 0-day juvenile antigens (These protein components can be separated by electrophoresis, in which case the total process can be described as immunoelectrophoresis). Antigen-antibody precipitates are thus formed. The precipitates are used to raise fresh antibody. For example, the precipitate can be injected into an animal of the same species, to raise an antiserum. This antibody then takes the place of the purified IgGs in the first embodiment.

While the invention is described herein by reference to *F. hepatica,* it will be appreciated that analogous steps can be taken for *F. gigantica,* the liver fluke to which domestic animals in Africa are most susceptible.

The starting crude 0-day juvenile antigenic extract can be obtained from metacercariae or cercariae.

The methods described herein for preparing the antigens have advantages over monoclonal screening methods (for production of stage-specific antigens) in that all stage-specific antigens in a population of Fasciola can be purified and characterised together. The invention includes any and all of the individual antigens obtainable by fractionation or purification of the JSA products. It is a simple matter to test any "doubtful" ones, by the method similar to that described in Example 1, stage 8 in which monoclonal antibodies are raised and the surface membrane of NEJs is tested for blistering.

It is believed that the antigens described herein are proteinaceous, but it is not certain whether the molecule consists entirely of peptide units or whether it also contains carbohydrate, lipid or other residues, or as to whether some of the antigens might contain no protein.

The invention includes also a fragment of an antigen of the invention carrying an antigenic determinant of specificity associated with the juvenile stage. Antigens and such fragments will be preparable by recombinant DNA technology or by other means. The invention includes in particular (1) a fragment obtained by manipulation of DNA coding for a protein comprised in an antigen of the invention and expression of the manipulated DNA and (2) fragment obtained by manipulation of enzymes or other organisms to construct non-proteinaceous residues or molecules of the antigen.

Also within the invention are antibodies to the juvenile-specific antigens of the invention, particularly monoclonal antibodies. These can be produced by any conventional hybridoma technology, e.g. that which proceeds by injecting the antigen into a suitable animal, e.g. a mouse or rat, or by a live infection of *Fasciola hepatica* and fusing appropriate animal cells, preferably spleen cells, with myeloma cells to form hybridoma cells, some of which will secrete antibodies to the antigen of the invention. The products are screened against juvenile and adult surfaces and sections of *F. hepatica* to select the monoclonals reactive to the juveniles alone.

Anti-idiotype antibody technology is advancing considerably and is the subject of several patent specifications. This provides a means of making polypeptides from carbohydrate-containing antigens. Anti-idiotype antibodies to epitopes (antigenic determinants) of antigens of the invention are included in the scope of the invention. They can be monoclonal or polyclonal.

The antigens and antibodies of the invention are of diagnostic value as components of assay kits, e.g. radioimmunoassay (RIA), enzyme-linked immunosorbent assay (ELISA), agglutination tests or indirect fluorescent antibody tests (IFAT), for detecting *F. hepatica* infection in sheep or cattle. It is believed that they will give an early signal of infection, for example so that it can be treated chemotherapeutically.

The antigens of the invention can be formulated into vaccines and the vaccines administered in any convenient conventional way and the invention accordingly provides a vaccine comprising an antigen of the invention alone or together with an adjuvant or carrier. A preferred adjuvant or carrier is of the aluminium hydroxide type such as "Alhydrogel". Desirably vaccination should be prophylactic. Preferably the vaccine is formulated as a "polyvalent" one to include as many individual JSAs or fragments of the invention as possible. A minor proportion by weight of adult antigen can also be included if desired.

It may be desirable to precede the administration of the vaccine by an appropriate priming injection, for example of a T-cell stimulant such as levamisole.

The following Examples illustrate the invention. "Amicon", "Sepharose" and "Tween" are Trade Marks.

EXAMPLE 1

1. Preparation of antigens

*Lymnaea truncatula* snails were infected, each with five miracidia hatched from *F. hepatica* eggs obtained from gall bladders of infected bovines from an abattoir in Dorset UK. Such eggs derived from infected bovines will have been transported from different parts of the UK via cattle markets. Metacercariae were shed from these snails and juveniles were hatched by the methods of D. V. M. Wickerhauser, Am. J. Vet. Res. 21, 895–897 (1960) and of M. M. H. Sewell & G. M. Purvis, Parasitology 59, 4P (abstracts) (1969). Juveniles were then separated from cyst materials by allowing them to migrate through nylon gauze of 30 micrometre mesh and then washing with phosphate buffered saline pH 7.6, homogenisation and sonication, all at 4° C. by the methods of C. E. Bennett et al., supra. (Spinning to remove cysts was not undertaken since no cysts are present in this procedure.) The antigen so produced is then designated 0-day juvenile antigen to indicate the stage immediately before infection of the vertebrate host.

2. Production of antiserum (AOJA)

The antigen used: 0-day juvenile antigen (above) was presented by inoculation in FCA to rabbits, as described by C. E. Bennett et al., supra. The antiserum thus produced was designated 'anti-0-day juvenile antiserum (AOJA)' (c.f. antimetacercarial antiserum (AMA) in C. E. Bennett et al., supra).

3. Absorption of AOJA with antigens of adult flukes

This method used was identical to that for the absorption of AMA in C. E. Bennett et al., supra. The adult *F. hepatica* lyophilate was obtained from Wistar rats infected with metacercariae derived from *Lymnaea truncatula* (originally infected with miracidia from the Dorset abattoir source). The ABS.-AOJA was cleaned by spinning at 1,900 G for 30 minutes at 4° C. and the supernatant passed through a 0.22 micrometre "Millipore" filter to remove immune complexes. The supernatant was termed absorbed anti-0-day juvenile antiserum (ABS.-AOJA) and contained antibodies specific to juvenile flukes, as shown by specific reaction in Ouchterlony double diffusion, immunoelectrophoresis and indirect fluorescent antibody tests.

4. Purification of antibodies to juvenile flukes

IgGs were extracted from the ABS.-AOJA prepared in stage 3 above by passing it down a protein A affinity column. Commercially available protein A-"Sepharose" Ch 4B beads (Pharmacia) were set up in a column and washed with 0.14 M phosphate buffer of pH 8.0 at 30 ml hr$^{-1}$.

ABS.-AOJA was then passed through the column until non-IgG specific serum components passed out as the drop-through fraction. IgGs bound to the column were subsquently eluted therefrom with 0.58% acetic acid. The IgGs were then neutralised with 1 M NaOH and dialysed against 22 mM phosphate-buffered saline. The IgGs were subjected to protein determination and tests for specific reactions by Ouchterlony double diffusion and immunoelectrophoresis.

5. Preparation of an affinity column of solid phase antibodies to juvenile flukes IgGs from ABS.-AOJA were bound to Sepharose 4B and set up as an affinity column. Cyanogen bromide-activated Sepharose 4B gel was swollen in 3 volumes of 1 mM HCl and after being gently spun down the HCl was withdrawn and the Sepharose remixed in coupling buffer (0.2 M NaHCO$_3$ containing 0.5 M NaCl pH 8.5). 12 ml of gel were then mixed with 90 mg IgGs in coupling buffer and binding of the IgGs was effected in an end-to-end turner overnight at 4° C., after which the gel was spun and coupling buffer removed. Remaining active groups on the gel were then blocked with 0.2 M glycine, followed by washing X 3 with 0.1 M acetate buffer, pH 4.0, containing 0.5 M NaCl and final washing in coupling buffer. The column was then packed with the IgGs of ABS.-AOJA and equilibrated by passing running buffer through the column at 7 ml/hour. The running buffer was 0.1 M phosphate buffer containing 0.3 M NaCl and 0.5% "Tween" 80.

6. Preparation of antigens of juvenile flukes

Crude 0-day juvenile antigen (prepared as described above in stage 1) was passed through the purified IgGs of ABS.-AOJA solid phase antibody column (prepared as described in stage 5 above) in the same phosphate running buffer as above and the crude antigen was cycled through the column three or more times before washing with running buffer until there was no further release of protein as measured at 280 nm. Bound antigens were then eluted with 3 M thiocyanate or 0.1 M glycine/HCl (each has been used successfully) at pH 2.5, dialysed against running buffer and subsequently concentrated on an "Amicon" membrane (molecular weight cut off 10,000) to remove low molecular weight material. The product comprised juvenile specific antigens (JSA).

7. Characterisation of juvenile specific antigens

Molecular weights were determined by two alternative methods as follows.

Method (a): on three occasions concentrated antigens were run in S.D.S. polyacrylamide gel by the method of U. K. Laemmli, Nature 277, 680 (1970) and stained with Coomasie blue.

Method (b): on one occasion concentrated antigens were iodinated with I$^{125}$ in iodosulphonic acid by the method of New England Nuclear (1983) and run in an S.D.S. polyacrylamide gel also by the method of U. K. Laemmli supra. Gels were dried and stained with Coomassie Blue and then autoradiographed with "Kodak" X-ray film XAR5 with a sensitivity filter.

Molecular weight standards run concurrently with juvenile specific antigens were

| Bovine Serum Albumin | MW 66,000 |
| Ovalbumin | MW 45,000 |
| Pepsin | MW 34,700 |
| Trypsinogen | MW 24,000 |
| Beta-lactoglobulin | MW 18,400 |
| Lysozyme | MW 14,300 |

Several protein bands were obtained by Method (a) from the JSA product obtained from three different batches of metacercariae. These had molecular weights as determined from three polyacrylamide gels of

| (i) | (ii) | (iii) |
| --- | --- | --- |
| 48,800 | 45,600 | 45,000 |
| 39,400 | 41,000 | 43,000 |

-continued

| (i) | (ii) | (iii) |
|---|---|---|
| 32,800 | 31,000 | 34,000 |
| 27,600 | | 30,000 |

By Method (b) molecular weights of 49,000; 34,300; 17,300; 15,600; and 11,900 were obtained from a further batch of metacercariae (iv).

The differing molecular weights are expainable by reference to the fact that the metacercariae emanated from eggs derived from infections from different parts of the UK.

8. Demonstration of antibody specificity for surface antigens

IgGs of ABS.-AOJA as recovered from the protein A column of stage 5, was applied in a concentration of 0.34 mg/ml in a defined medium to NEJ (in vitro hatched) *F. hepatica*. Prominent blistering of the surface membrane of the tegument occurred within 1 hour of application. The immune reaction led also to a form of focal capping of the membrane into flocculant microvillar formations. This is ascribed to a lattice formation of IgGs cross-linking with surface antigens.

9. Use of the JSA product in vaccination against liver fluke

Four groups of 10 three week old female Wistar rats were used.

Group I was a control group which was not vaccinated prior to infection.

Group II was a control group which was sham-vaccinated with saline and FCA at the intervals shown below identical to those in group III.

Group III was vaccinated with JSA product of Example 1, stage 6 in FCA until there was a detectable serological response by Ouchterlony Double Diffusion. The JSAs emanated from metacercariae of batches (ii) and (iii). The doses of antigen followed a regime devised to minimise the use of antigen. The tails of the rats were bled 6 days after the second and third immunisations to provide samples.

Group IV was an uninfected group for collection of control sera for a glutamate dehydrogenase (GLDH) assay in order to assess liver damage.

First immunisation—Rat age 24 days 90 micrograms JSA product in 0.5 ml FCA/PBS (1:1 volume) 0.3 ml intraperitoneally, 0.2 ml into the flanks.

Second immunisation—Rat age 44 days

As above but only 40 micrograms of the JSA product.

Third immunisation—Rat age 59 days

As above but 80 micrograms of the JSA product.

A strong detectable serological response was given by the Group III rats after 66 days. All three groups were then infected with 20 metacercariae from a random batch.

Blood was taken from all rats for serum Glutamate Dehydrogenase (GLDH) assay at 28 days p.i.

Necropsy for a count of mature worms in the bile ducts was carried out at 70 day p.i.

The data in Tables 1 and 2 below were analysed in terms of % protection and by comparison of the groups by the Mann-Whitney U-test.

TABLE 1

Number of *Fasciola hepatica* adults recovered by necropsy

| Group I control | Group II sham vaccinated | Group III vaccinated |
|---|---|---|
| 2 | 3 | 2 |
| 4 | 4 | 2 |
| 2 | 8 | 4 |
| 2 | 1 | 0 |
| 5 | 2 | 0 |
| 5 | 7 | 0 |
| 2 | 5 | 2 |
| 6 | 1 | 0 |
| 4 | 4 | 1 |
| 3 | 2 | 2 |
| Totals 35 | 37 | 13 |

$$\% \text{ Protection} = \frac{(\text{Mean number control flukes}) - (\text{Mean number vaccinated flukes}) \times 100}{\text{Mean number control flukes}}$$

Testing group II against Group I: $\frac{35 - 13}{35} = 63\%$ Protection

Testing Group II against Group I: $\frac{37 - 13}{37} = 65\%$ Protection

Mann-Whitney U-tests — Testing Group I against Group III, the test is significant at 0.0073. Testing Group II against Group III, the test is significant at 0.0211.

TABLE 2

Liver damage at 28 days p.i. as assayed by GLDH assay Readings in Units/Liter

| | Group I control | Group II sham vaccinated | Group III vaccinated | Group IV uninfected |
|---|---|---|---|---|
| | 255.0 | 342.5 | 187.5 | 15.0 |
| | 245.0 | 167.5 | 87.5 | 10.0 |
| | 187.5 | 315.0 | 142.5 | 10.0 |
| | 197.5 | 337.5 | 132.5 | 30.0 |
| | 195.0 | 122.5 | 60.0 | 20.0 |
| | 197.0 | 202.5 | 35.0 | 40.0 |
| | 192.0 | 127.5 | 0.0 | 0.0 |
| | 242.5 | 202.5 | 187.0 | 25.0 |
| | 167.5 | 142.5 | 15.0 | 25.0 |
| | 225.0 | 210.5 | 10.0 | 20.0 |
| Mean | 210.4 | 217.0 | 85.7 | 19.5 |
| Corrected mean | 190.9 | 197.5 | 66.2 | 0 |

% Protection = (Corrected mean number Units Control) − (Corrected mean number Units Vaccinated) × 100 Mean number Units Control = 66%

Mann-Whitney U-tests — Testing Group I against Group III, the test is significant at 0.0004. Testing Group II against Group III, the test is significant at 0.0052.

EXAMPLE 2

ABS.-AOJA, produced as in Example 1, stages 1, 2, and 3, was run in immunoelectrophoresis by the methods of C. E. Bennett et al., supra, against crude 0-day juvenile antigen of *F. hepatica* prepared as in Example 1, stage 1. In other words, 10 microliters of the 0-day juvenile antigen were electrophoresed at 10 V cm$^{-1}$ for 90 minutes. Then 100 microliters of the ABS.-AOJA were pipetted into the adjoining trough and the diffusion reaction was allowed to proceed for 24 hours. Arcs resulting from precipitation overnight of the antigen-antibody complex were excised from the plates. Arcs 1 and 2 together and Arc 3 on its own (in agar) were respectively washed in several changes of PBS over 6–8 weeks. The more prominent band was that of Arc 3, which was reinoculated into rabbits with FCA by the method of C. E. Bennett et al., supra. The antisera were collected and tested for positive reaction with 0-day juvenile antigen by Ouchterlony double diffusion and immunoelectrophoresis. Positive antisera were saved for use in affinity chromatography (below).

Immunoglobulins were bound to Sepharose 4B and set up as an affinity column as in Example 1, stage 5.

Crude 0-day juvenile antigen prepared as in Example 1, stage 1 was run through the affinity column and the bound antigens eluted, all as described in Example 1, stage 6.

Molecular weights of JSAs produced from the affinity column were determined as described in Example 1, stage 7. By Method (a), on the JSA product from one batch of metacercariae, molecular weight of 61,700; 59,000; 51,500; 44,700; 32,000 and 26,500 were obtained. By Method (b), on the JSA product from another batch of metacercariae, molecular weights of 49,000; 41,700 and 13,200 were obtained.

The molecular weights 49,000; 44,700; 41,700 and 32,000 correspond approximately to those for juvenile specific antigens in Example 1. The 26,500 and 13,200 molecular weights are possibly of antigens common to adults and juveniles.

The product of Example 2 was shown by ELISA to react with serum obtained from rats infected with *F. hepatica*, at 26 days post infection. This is both the earliest stage at which rats infected with *F. hepatica* exhibit a resistance to reinfection and the earliest stage at which antibodies to juvenile specific antigens are detectable in the rat.

I claim:

1. An antigen specific to the juvenile state of Fasciola and extracted from juvenile Fasciola organisms by separating said juvenile organisms from metacercarial cysts of Fasciola, raising an antiserum to the juvenile organisms, absorbing this antiserum with antigens extracted from adult Fasciola organisms, thereby forming an adult antigen—adult antibody complex and leaving other components of the antiserum unabsorbed, separating immunoglobulin components of the unabsorbed antiserum from the adult antigen - adult antibody complex, insolubilising the immunoglobulins, purifying crude juvenile Fasciola antigens by reacting them with the insolubilised immunoglobulins to form an antigen-antibody complex and liberating a juvenile-specific antigen from the complex.

2. An antigen sepcific to the juvenile stage of Fasciola and extracted from juvenile Fasciola organisms by separating said juvenile organisms from metacercarial cysts of Fasciola, raising an antiserum to the juvenile organisms, absorbing this antiserum with antigens extracted from adult Fasciola organisms, thereby forming an adult antigen—adult antibody complex and leaving other components of the antiserum unabsorbed, reacting the unabsorbed antiserum with crude juvenile Fasciola antigens, to form a first juvenile antigen - juvenile antibody complex, raising an antiserum against the antigenic component of this complex, insolubilising the antibodies thereby produced, and purifying curde juvenile Fasciola antigens by reacting them with the insolubilised antibodies to form a second juvenile antigen - juvenile antibody complex, and liberating a juvenile-specific antigen from the complex.

3. An antigen according to claim 1 wherein the species of Fasciola is *Fasciola hepatica*.

4. An antigen according to claim 2 wherein the species of Fasciola is *Fasciola hepatica*.

5. A fragment of an antigen claimed in claim 1 carrying at least one antigenic determinant specific to the juvenile stage of the Fasciola species.

6. A fragment of an antigen claimed in claim 2 carrying at least one antigenic determinant specific to the juvenile stages of the Fasciola species.

7. And polyclonal antibodies to an antigen claimed in claim 1.

8. A fragment of an antigen claimed in claim 2 carrying at least one antigenic determinant specific to the juvenile stage of the Fasciola species.

9. A fragment of an antigen claimed in claim 3 carrying at least one antigenic determinant specific to the juvenile stage of the Fasciola species.

10. A fragment of an antigen claimed in claim 4 carrying at least one antigenic determinant specific to the juvenile stage of the Fasciola species.

11. Monoclonal and polyclonal antibodies to an antigenic fragment claimed in claim 5.

12. Monoclonal and polyclonal antibodies to an antigenic fragment claimed in claim 6.

13. A vaccine for use in inoculating vertebrate animals against Fasciola, comprising an antigen claimed in claim 1 together with an adjuvant or carrier.

14. A vaccine for use in inoculating vertebrate animals against Fasciola, comprising an antigen claimed in claim 2 together with an adjuvant or carrier.

15. A vaccine for use in inoculating vertebrate animals against Fasciola, comprising an antigen claimed in claim 3 together with an adjuvant or carrier.

16. A vaccine for use in inoculating vertebrate animals against Fasciola, comprising an antigen claimed in claim 4 together with an adjuvant or carrier.

17. A vaccine for use in inoculating vertebrate animals against Fasciola, comprising an antigenic fragment claimed in claim 5 together with an adjuvant or carrier.

18. A vaccine for use in inoculating vertebrate animals against Fasciola, comprising an antigenic fragment claimed in claim 6 together with an adjuvant or carrier.

19. A method of vaccinating vertebrate animals against Fasciola, comprising administering to an animal susceptible to invasion by Fasciola an antigen claimed in claim 1.

20. A method of vaccinating vertebrate animals against Fasciola, comprising administering to an animal susceptible to invasion by Fasciola an antigen claimed in claim 2.

21. A method of vaccinating vertebrate animals against Fasciola, comprising administering to an animal susceptible to invasion by Fasciola an antigen claimed in claim 3.

22. A method of vaccinating vertebrate animals against Fasciola, comprising administering to an animal susceptible to invasion by Fasciola an antigen claimed in claim 4.

23. A method of vaccinating vertebrate animals against Fasciola, comprising administering to an animal susceptible to invasion by Fasciola an antigenic fragment claimed in claim 5.

24. A method of vaccinating vertebrate animals against Fasciola, comprising administering to an animal susceptible to invasion by Fasciola an antigenic fragment claimed in claim 6.

25. Antibodies to an antigen claimed in claim 10.

* * * * *